United States Patent [19]
Fujitani et al.

[11] Patent Number: 5,517,425
[45] Date of Patent: May 14, 1996

[54] METHOD OF DISCRIMINATING EQUILIBRIUM CHARACTERISTICS OF HYDROGEN ABSORBING ALLOYS

[75] Inventors: Shin Fujitani, Hirakata; Akio Furukawa, Osaka; Ikuo Yonezu, Hirakata; Toshihiko Saito, Tsuzuki, all of Japan

[73] Assignee: Sanyo Electric Co., Ltd., Moriguchi, Japan

[21] Appl. No.: 305,802

[22] Filed: Sep. 13, 1994

Related U.S. Application Data

[63] Continuation of Ser. No. 941,803, Sep. 8, 1992, abandoned.

[30] Foreign Application Priority Data

Sep. 30, 1991 [JP] Japan .................. 3-251381

[51] Int. Cl.$^6$ .............. G01N 7/00; G06F 19/00
[52] U.S. Cl. .................. 364/496; 364/499
[58] Field of Search ............. 364/496, 497, 364/499, 578, 580

[56] References Cited

FOREIGN PATENT DOCUMENTS

| 57-47854 | 3/1982 | Japan . |
| 61-286735 | 12/1986 | Japan . |
| 63-430 | 1/1988 | Japan . |

OTHER PUBLICATIONS

Oates, "Thermodynamic Properties of the Pd–H System", Journal of the Less–Common Metals, 88, pp. 411–424, The Netherlands, 1982.

Flangan et al., "Hysteresis in Metal Hydrides", Journal of the Less–Common Metals, 83, pp. 127–141, The Netherlands, 1982.

"A Numerical Method for the P–C–T Properties of Metal Hydrides", H. Bjurström et al., Journal of the Less–Common Metals, vol. 130, Mar. 1, 1978, pp. 365–370.

"A Theoretical Formula for the Solubility of Hydrogen in Palladium", John R. Lacher, Proceedings of the Royal Society of London (Series A–Mathematical and Physical Sciences), vol. 161, Aug. 20, 1937, pp. 525–545.

Fujitani et al., "Formulation for Pressure Composition Isotherms of Hydrogen in Hydrogen Absorbing Rare Earth–Ni Alloys/Y, Mn Substitution Effect of Hydrogen Equilibrium Characteristics of Hydrogen–Absorbing Rare Earth–Nickel Alloys", Journal of the Japan Institute of Metals, V. 56, N. 8, 1992 pp. 965–972.

Primary Examiner—Ellis B. Ramirez
Assistant Examiner—M. Kemper
Attorney, Agent, or Firm—Armstrong, Westerman, Hattori, McLeland & Naughton

[57] ABSTRACT

The plateau region of P-C-T isotherm of a hydrogen absorbing alloy between the $\alpha$ phase region and $\beta$ phase region thereof is expressed by a normal cumulative distribution function wherein hydrogen content X is taken as frequency and the logarithm of equilibrium hydrogen pressure as a random variable. Parameters such as standard deviation $\sigma$ of the function are determined by numerical analysis based on measured data as to the equilibrium hydrogen pressure and hydrogen content of the plateau region of the alloy to be evaluated. Whether the equilibrium characteristics of the alloy are acceptable is determined using the parameters as evaluation criteria.

7 Claims, 8 Drawing Sheets

| modeling parameter | as cast | as annealed |
|---|---|---|
| $Xs/(mol\ M)^{-1}$ | 1.112 | 1.114 |
| $X\alpha\ /(mol\ M)$ | 0.114 | 0.086 |
| $X\beta\ /(mol\ M)$ | 0.890 | 0.936 |
| $(X\beta - X\alpha)\ /\ (mol\ H/mol\ H)$ | 0.776 | 0.850 |
| $f_1$ | 1.00 | 1.00 |
| $\sigma_1/10^{-2}$ | 4.0 | 0.3 |
| $Pm_1/MPa$ | 0.193 | 0.190 |

| modeling parameter | aloy as cast | alloy as annealed |
|---|---|---|
| $X_s/(\text{mol M})^{-1}$ | 1.054 | 1.077 |
| $X_\alpha/(\text{mol M})$ | 0.110 | 0.069 |
| $X_\beta/(\text{mol M})$ | 0.880 | 0.867 |
| $(X_\beta - X_\alpha)/(\text{mol H/mol M})$ | 0.770 | 0.798 |
| $f_1$ | 1.00 | 1.00 |
| $\sigma_1/10^{-2}$ | 28.8 | 6.3 |
| $P_{m1}/\text{MPa}$ | 0.090 | 0.125 |

| modeling parameter | alloy as cast |
|---|---|
| $f_1$ | 0.30 |
| $\sigma_1/10^{-2}$ | 19.2 |
| $Pm_1$/MPa | 0.062 |
| $f_2$ | 0.70 |
| $\sigma_2/10^{-2}$ | 18.1 |
| $Pm_2$/MPa | 0.103 |

| modeling parameter | alloy as cast | alloy as annealed |
|---|---|---|
| $X_s/(\text{mol M})^{-1}$ | 1.006 | 1.096 |
| $X_\alpha/(\text{mol M})$ | 0.124 | 0.088 |
| $X_\beta/(\text{mol M})$ | 0.470 | 0.845 |
| $(X_\beta - X_\alpha)/(\text{mol H/mol M})$ | 0.346 | 0.757 |
| $f_1$ | 1.00 | 1.00 |
| $\sigma_1/10^{-2}$ | 5.4 | 10.6 |
| $P_{m1}/\text{MPa}$ | 0.506 | 0.579 |

5,517,425

1

METHOD OF DISCRIMINATING EQUILIBRIUM CHARACTERISTICS OF HYDROGEN ABSORBING ALLOYS

This application is a continuation of application Ser. No. 07/941,803 filed Sep. 8, 1992, now abandoned.

FIELD OF THE INVENTION

The present invention relates to a method of discriminating the equilibrium characteristics of hydrogen absorbing alloys for the determination of acceptability by modeling the pressure-composition isotherms (P-C-T isotherms) of such alloys which represent the relation between the equilibrium hydrogen pressure P and the hydrogen content C using the temperature T as a parameter.

BACKGROUND OF THE INVENTION

Clean hydrogen has attracted attention in recent years as an energy source substituting for fossil fuels owing to the warming of global climate due to $CO_2$.

In view of this situation, attention has been directed to hyrogen absorbing alloys as novel functional materials. These alloys include two-component alloys, such as $ZrMn_2$, $TiMn_2$, $TiCr_2$, $Mg_2Ni$, $TiFe$ and $LaNi_5$, which are safe and easy to handle and which have reversible reactivity with hydrogen at pressure levels of 0.1 to 1 MPa, and quasi two-component alloys resembling such alloys and comprising more components.

Hydrogen absorbing alloys perform outstanding functions in converting energy and purifying hydrogen and are regarded as functional materials which are indispensable to the efficient use of hydrogen energy, for example, for use in storing or transporting hydrogen or in heat pumps utilizing the reaction heat thereof.

The equilibrium reaction between the hydrogen absorbing alloy and hydrogen is evaluated with reference to a hydrogen pressure-composition (hydrogen content) isotherm (P-C-T isotherm).

Figure 3:
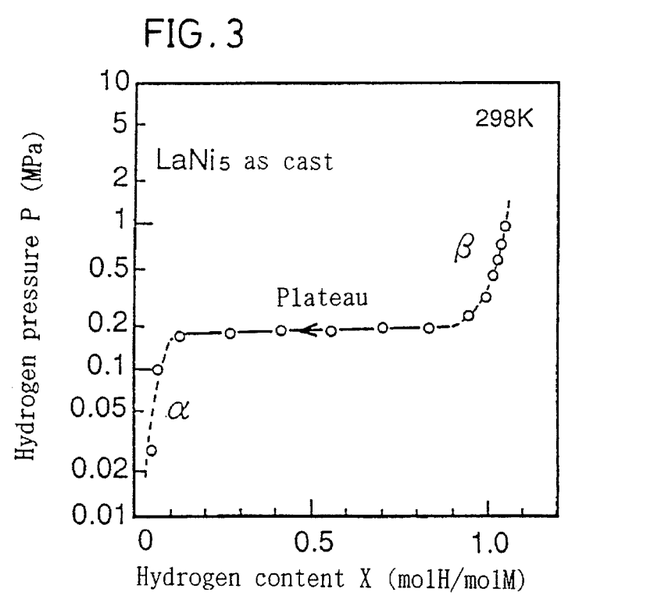
FIG. 3 is a P-C-T characteristics diagram showing the result obtained with a first sample as cast.

For example, FIG. 3 shows a P-C-T isotherm of $LaNi_5$ which is a hydrogen absorbing alloy at a temperature of 298K. With reference to the diagram wherein the hydrogen content is plotted as abscissa vs. the equilibrium hydrogen pressure as ordinate, the P-C-T isotherm has a hydrogen solid solution region ($\alpha$ phase region) and a metal hydride region ($\beta$ phase region) which are great in gradient, and a generally horizontal plateau region between the two regions.

Especially, the width of the plateau region corresponds to the content of hydrogen which is effectively movable in the system. The greater the value of effective hydrogen content, the smaller is the amount of alloy needed and the system can be more efficient and smaller in size.

The plateau region is a region where three phases are conjointly present. According to Gibbs' phase rule, this region is a horizontal portion exhibiting a constant pressure independently of the composition of the hydrogen absorbing alloy. In the actual metal-hydrogen reaction, however, this portion has a positive inclination due to the heterogeneity of the alloy from the viewpoint of metal engineering.

For example when the hydrogen absorbing alloy is applied to heat accumulation systems, a very great disadvantage will result with respect to efficiency if the plateau region has a great inclination since the hydrogen content due to a given pressure difference is then small. For this reason,

2 efforts are made to render the plateau region horizontal as by making the alloy homogeneous by heat treatment.

Accordingly, modeling of P-C-T isotherms, if possible, is very significant because the models are not only useful for designing various application systems wherein hydrogen absorbing alloys are used, simulated operation of such systems and evaluation thereof but also permit accumulation and use of equilibrium characteristics data of various alloys to provide guides in designing and developing more efficient alloys.

Heretofore known as modeling P-C-T isotherms are formulation based on a regular solution model in Pd-H system ("A Theroretical Formula for the Solubility of Hydrogen in Palladium," R. Soc. London, Ser A.161 (1937), pp. 525–545) and formulation based on adsorption isothermal formula of the Langmuir type in $LaNi_{4.79}Al_{0.21}$—H sytstem ("A NUMERICAL EXPRESSION FOR THE P-C-T PROPERTIES OF METAL HYDRIDES," Journal of the Less-Common Metals, 130(1987), pp. 365–370).

However, the former has the drawback of being unable to fully express the inclination of the plateau although capable of accurately exressing the hydrogen solid solution region ($\alpha$ phase region) and metal hydride region ($\beta$ phase region).

On the other hand, the latter is capable of expressing the overall P-C-T isotherm region almost satisfactorily, but the parameters included in the expression have no physicochemical meaning, the P-C-T isotherm being merely modeled by numerical analysis, so that it is not reasonable to use the parameter obtained by modeling for the evaluation of the equilibrium characteristics of the hydrogen absorbing alloy.

SUMMARY OF THE INVENTION

An object of the present invention is to model the plateau region of a P-C-T isotherm of a hydrogen absorbing alloy by a relational expression including parameters having physicochemical meanings and provide a method of discriminating the equilibrium characteristics of the alloy using the parameters as evaluation criteria.

Directing attention to the fact that the inclination of the plateau region is attributable to the heterogeneity of the alloy phase to fulfill the above object, we have accomplished the present invention based on the novel and reasonable concept of using a cumulative distribution function as means for expressing the heterogeneity in modeling the plateau region.

In discriminating the equilibrium characteristics of a hydrogen absorbing alloy, the present invention provides a method of determining the acceptability of the equilibrium characteristics of a plateau region of the hydrogen absorbing alloy between a hydrogen solid solution region ($\alpha$ phase region) thereof and a metal hydride region ($\beta$ phase region) thereof, the method comprising the step of measuring the equilibrium hydrogen pressure and hydrogen content of the plateau region of the alloy, the step of expressing the plateau region by a cumulative distribution function wherein the hydrogen content is taken as frequency and the equilibrium hydrogen pressure or a function thereof is taken as a random variable and determining a plurality of parameters defining the cumulative distribution function by numerical analysis of measured data as to the equilibrium hydrogen pressure and the hydrogen content, the step of outputting the determined parameters, and the step of determining whether the equilibrium characteristics are acceptable using the output parameters as evaluation criteria.

A normal cumulative distribution function can be used as the cumulative distribution function. In this case, the logarithm of the equilibrium hydrogen pressure is taken as a random variable, and the standard deviation of the normal cumulative distribution function is used as an evaluation criterion.

The plateau region of the hydrogen absorbing alloy can be expressed as a linear combination of a plurality of cumulative distribution functions. In this case, a weighting coefficient for each of the cumulative distribution functions can be added to the evaluation criterion.

Further the boundaries between the plateau region of the hydrogen absorbing alloy and the hydrogen solid solution region and the metal hydride region thereof can be determined by a regular solution model. In this case, the hydrogen content at a boundary point serves as another evaluation criterion.

Various numerical analytical methods, such as the least square method, are usable as the method of determining a plurality of parameters defining the cumulative distribution function, based on the measured data as to the equilibrium hydrogen pressure and the hydrogen content of the plateau region of the hydrogen absorbing alloy to be evaluated.

In the present method of discriminating the equilibrium characteristics of the hydrogen absorbing alloy, the inclination of the plateau region due to metallurgical heterogeneity of the alloy phase is modeled by a cumulative distribution function serving as means for expressing the heterogeneity, so that the parameters of the function have physicochemical meanings representing the basic characteristics of the plateau region.

Use of the parameters as evaluation criteria therefore makes it possible to prevalently express the equilibrium characteristics of the hydrogen absorbing alloy.

DETAILED DESCRIPTION OF EMBODIMENTS

Figure 1:
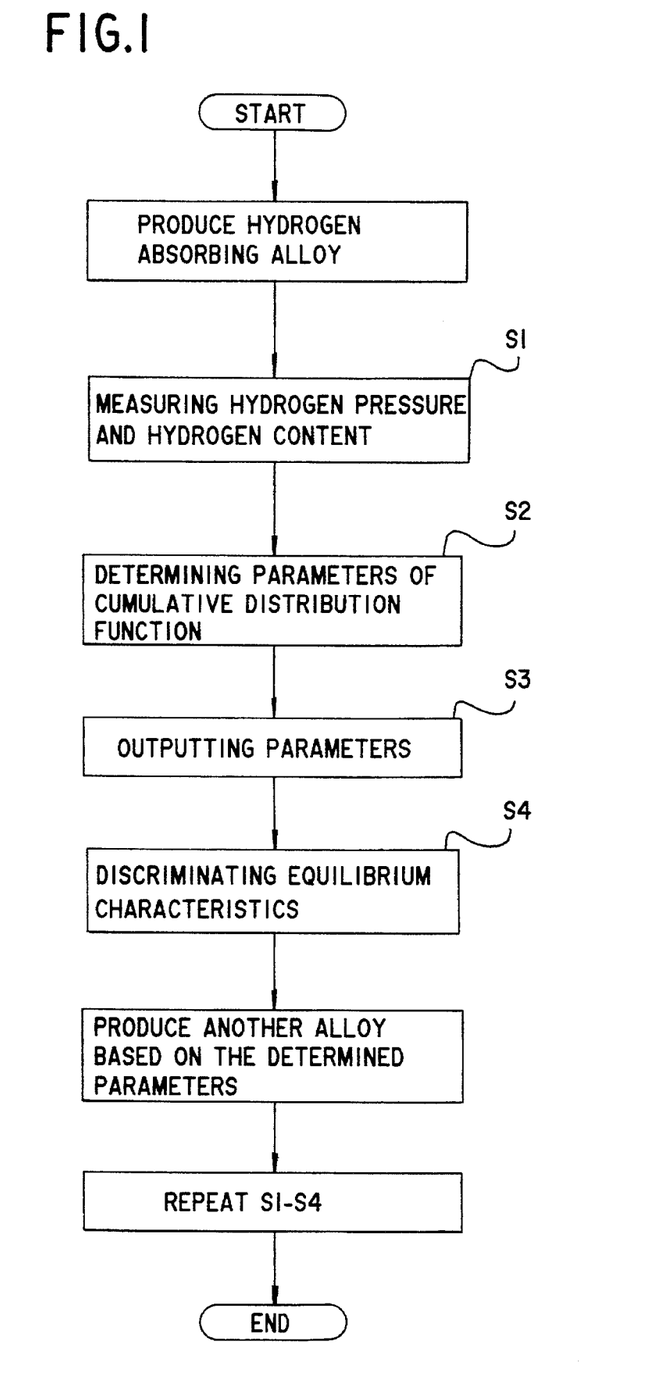
FIG. 1 is a flow chart showing the steps of a method embodying the invention for discriminating the equilibrium characteristics of a hydrogen absorbing alloy.

FIG. 1 shows the basic steps of the method of the present invention for discriminating the equilibrium characteristics of hydrogen absorbing alloys. The method comprises producing a hydrogen absorbing alloy, the step S1 of measuring the equilibrium hydrogen pressure and hydrogen content of the plateau region of the alloy, the step S2 of expressing the plateau region by a cumulative distribution function wherein the hydrogen content is taken as frequency and the equilibrium hyrogen pressure or a function thereof is taken as a random variable and determining a plurality of parameters defining the cumulative distribution function by numerical analysis of measured data as to the equilibrium hydrogen pressure and the hydrogen content, the step S3 of outputting the determined parameters, and the step S4 of determining whether the equilibrium characteristics are acceptable using the output parameters as evaluation criteria producing another alloy based on the determined parameters, and repeating steps S1–S4.

Embodiments will be described below where P-C-T isotherms are modeled with use of normal cumulative distribution function including the hydrogen content as the frequency and the logarithm of the equilibrium hydrogen pressure as a random variable, and the hydrogen solid solution phase and the hydride phase are modeled with use of a regular solution model.

Used as hydrogen absorbing alloys in these embodiment were typical examples of $AB_5$ type rare earth metal-Ni alloys, i.e., a two-component alloy $LaNi_5$, and quasi two-component alloys $La_{0.8}Y_{0.2}Ni_5$ and $LaNi_{4.8}Mn_{0.2}$ which were obtained by partly substituting La or Ni of the alloy with Y or Mn which has a great effect to increase or decrease the equilibrium hydrogen pressure as an important property of useful materials. The alloys were checked for the relation between variations in P-C-T isotherm modeling parameters resulting from annealing and the corresponding changes in the alloy structure.

Method of Producing the Alloys

The alloys were produced each by preparing a specified mixture from Ni and Mn having a purity of 99.9% and La and Y having a purity of 99% and melting the mixture using an argon arc furnace.

The ingot, obtained in the form of a button, was divided into two pieces. One of them was used as cast (alloy as cast), and the other piece was enclosed in a quartz tube and annealed in a vacuum at a temperature of 1273K for 8 hours to obtain an anealed alloy (alloy as annealed). These alloys were used for determining the P-C-T isotherm thereof and for analysis.

Method of Determining P-C-T Characteristics

The P-C-T characteristics of the alloy were determined by the volumetric method using Sievert's device. The sample was pulverized to about 100-mesh size and enclosed in a stainless steel reactor. The hydrogen gas used was 5N high-purity gas.

For initial activation, the alloy was subjected to 5 repeated cycles of evacuation to a vacuum at a temperature of 363K by a rotary pump and application of hydrogen to a pressure of 1 MPa at a temperature of 298K. Before the determination, the alloy was evacuated to a vacuum at a temperature of 323K for 1 hour by the rotary pump to set the origin for hydrogen contents.

For modeling, all the measurements were obtained at a temperature of 25° C. (298K), and hydrogen desorbing curves were accurately determined with the hydrogen content X plotted at an interval of up to 0.15. The hydrogen content X was expressed in the ratio of the number of hydrogen atoms to the number of metal atoms in the alloy (mol H/mol M).

Analysis Method

Further to investigate the relation between the inclination of the plateau region and the heterogeneity of the alloy phase, the alloy structure was observed by electron beam probe microanalysis (EPMA).

In EPMA, distribution of alloy component elements were determined by plane analysis and elemental mapping.

Next, P-C-T isotherms were modeled by the method to be described below. Tables 1 to 3 collectively show the variables to be used in the following method, and the physical meanings and units thereof.

TABLE 1

| Fitting region | Variable | Physical meaning | Unit |
|---|---|---|---|
| Overall region | P | Equilibrium hydrogen pressure | Pa |
| | Pt | Plateau pressure when plateau has no inclination (measured at midpoint of plateau region) | Pa |
| | $P_0$ | Unit pressure | Pa |
| | X | Hydrogen content | mol H/mol M |
| | T | Temperature (alloy temperature) | K |
| | R | Gas constant | J/(K · mol) |

TABLE 2

| Fitting region | Variable | Physical meaning | Unit |
|---|---|---|---|
| α and β regions | $\mu_H$ | Chemical potential of hydrogen in alloy | J/mol H |
| | $\mu_H^\circ$ | Value of $\mu_H$ in standard state | J/mol H |
| | $\mu_{H2}^\circ$ | Value of $\mu_{H2}$ in standard state | J/mol H |
| | $\Delta\mu^\circ$ | $= \mu_H^\circ - \frac{1}{2}\mu_{H2}^\circ$ | J/mol H |
| | Xs | Number of hydrogen sites in alloy (maximum hydrogen content) | mol M$^{-1}$ |
| | $X_\alpha$ | α phase boundary | mol H/mol M |
| | $X_\beta$ | β phase boundary | mol H/mol M |
| | $E_{HH}$ | Interaction energy of hydrogen in alloy | J · mol M/mol H |

TABLE 3

| Fitting region | Variable | Physical meaning | Unit |
|---|---|---|---|
| Plateau region | φ | Normal cumulative distribution function | — |
| | a | Linear incidence number | mol H/mol M |
| | f | Fractions of two normal cumulative distribution functions | — |
| | m | Mean value (natural logarithmic scale of pressure) | — |
| | Pm | $= P_0 \exp [m]$ | Pa |

TABLE 3-continued

| Fitting region | Variable | Physical meaning | Unit |
|---|---|---|---|
| | σ | Standard deviation | — |

In the above tables, mol H refers to mol hydrogen, and mol M to mol metal.

For modeling the plateau region, it is first necessary to reasonably determine the boundaries of the plateau region, i.e., α phase region (Xα) and β phase region (Xβ). For this purpose, the aforementioned regular solution model is used. This model is usable not only for determining the boundaries but also for modeling the α phase and β phase.

Modeling of β and β Phases and Determination of Phase Boundaries with Regular Solution Model With the regular solution model, equilibrium between hyrogen in the gas phase and hydrogen in the alloy is expressed by Equation 1, which means that the chemical potential of the gas phase and the chemical potential of hydrogen in the alloy (regular solution model) are equal.

$$\mu_H = \frac{1}{2}\left(\mu_{H2}^\circ + RT \times \ln\frac{P}{P_0}\right) = \mu_H^\circ + RT \times \ln\frac{X}{Xs-X} - E_{HH}X \quad \text{(Equation 1)}$$

wherein $\mu_{H2}^\circ$ is standard chemical potential of hydrogen gas, P is hydrogen pressure, $P_0$ is a reference value of pressure (=0.1 MPa), R is a gas constant, T is temperature, S is entropy, H is enthalpy, $\mu_H^\circ$ is standard chemical potential of hyrogen in the alloy, Xs is a maximum hydrogen content (number of effective hydrogen sites), $E_{HH}$ is energy of interaction of hydrogen in the alloy, and X is hydrogen content.

Equation 1 affords Equation 2, which basically shows the relation between the hydrogen pressure P, hydrogen content X and temperature T, i.e., P-C-T isotherm. Incidentally, $\Delta\mu^\circ$ and $E_{HH}$ involve dependency as represented by Equations 3 and 4.

$$\ln\frac{P}{P_0} = \frac{2\Delta\mu^\circ}{RT} + 2 \times \ln\frac{X}{Xs-X} - \frac{2E_{HH}}{RT}X \quad \text{(Equation 2)}$$

$$\Delta\mu^\circ = \mu_H^\circ - \frac{1}{2}\mu_{H2}^\circ = H\mu - TS\mu \quad \text{(Equation 3)}$$

$$E_{HH} = H_{HH} - TS_{HH} \quad \text{(Equation 4)}$$

A description will now be given of the case wherein parameters are determined from one item of temperature data.

With reference to Equation 5 derived from Equation 2 and given below, a straight line having a slope of $-2E_{HH}/RT$ and an intercept of $2\Delta\mu^\circ/RT$ is obtained by plotting the value of the left side against the value of X on the right side. Accordingly, determination of Xs at which the sum of residual squares is smallest by the least square method gives $E_{HH}$ and $\Delta\mu^\circ$ from the intercept and the slope at this time.

$$\ln\frac{P}{P_0} - 2 \times \ln\frac{X}{Xs-X} = \frac{2\Delta\mu^\circ}{RT} - \frac{2E_{HH}}{RT}X \quad \text{(Equation 5)}$$

Next, a description will be given of the case wherein parameters are determined from at least two items of temperature data.

Equation 6 given below is obtained from Equations 2, 3 and 4.

$$\ln \frac{P}{P_0} = 2 \times \ln \frac{X}{Xs-X} = \quad \text{(Equation 6)}$$

$$\frac{2H\mu}{R} \cdot \frac{1}{T} - \frac{2S\mu}{R} - \frac{2H_{HH}}{R} \cdot \frac{X}{T} + \frac{2S_{HH}}{R} X$$

Equation 6 can be expressed in a linear form as represented by Equation 8 by converting the variables as expressed by Equations 7 below.

$$y = \ln \frac{P}{P_0} - 2 \times \ln \frac{X}{Xs-X} \quad \text{(Equations 7)}$$

$$x_1 = \frac{1}{T}$$

$$x_2 = \frac{X}{T}$$

$$x_3 = X$$

$$a_0 = \frac{2S\mu}{R}$$

$$a_1 = \frac{2H\mu}{R}$$

$$a_2 = -\frac{2H_{HH}}{R}$$

$$a_3 = \frac{2S_{HH}}{R}$$

(Equation 8

$$y = a_0 + a_1 x_1 + a_2 x_2 + a_3 x_3$$

Thus, $a_0$, $a_1$, $a_2$ and $a_3$ can be determined using actually measured data $X_1$, $X_2$ and $X_3$. In this case, $a_0$, $a_1$, $a_2$ and $a_3$ are determined also for Xs at which the sum of residual squares is smallest.

In this way, the parameters included in Equation 2 are determined from actual measurements to model the relation between the pressure P and the hydrogen content X at the specified temperature T, i.e., pressure-composition (hydrogen content) isotherm.

Since the α phase and β phase usually have different parameters, Equations 9 and 10 are obtained by individual analysis.

$$\ln \frac{P}{P_0} = \frac{2\Delta\mu_\alpha^\circ}{RT} + 2 \times \ln \frac{X}{X_{s,\alpha}-X} - \frac{2E_{HH,\alpha}}{RT} X \quad \text{(Equation 9)}$$

$$X = \theta_\alpha \left( \ln \frac{P}{P_0} ; \Delta\mu_\alpha^\circ, X_\alpha, E_{HH,\alpha} \right)$$

$$\ln \frac{P}{P_0} = \frac{2\Delta\mu_\beta^\circ}{RT} + 2 \times \ln \frac{X}{X_{s,\beta}-X} - \frac{2E_{HH,\beta}}{RT} X \quad \text{(Equation 10)}$$

$$X = \theta_\beta \left( \ln \frac{P}{P_0} ; \Delta\mu_\beta^\circ, X_\beta, E_{HH,\beta} \right)$$

Now, the phase boundaries are determined from Equations 11 and 12 using actually measured data, i.e., the pressure Pt at the midpoint of the plateau region.

$$\ln \frac{Pt}{P_0} = \frac{\Delta\mu_\alpha^\circ}{RT} + 2 \times \ln \frac{X_\alpha}{X_{s,\alpha}-X_\alpha} - \frac{2E_{HH,\alpha}}{RT} X_\alpha \quad \text{(Equation 11)}$$

$$\ln \frac{Pt}{P_0} = \frac{\Delta\mu_\beta^\circ}{RT} + 2 \times \ln \frac{X_\beta}{X_{s,\beta}-X_\beta} - \frac{2E_{HH,\beta}}{RT} X_\beta \quad \text{(Equation 12)}$$

Thus, it is thought that if the plateau has no inclination, the pressure Pt gives rise to α-β transformation (formation or decomposition of β hydrogen compound phase from α solid solution phase).

Modeling of the Plateau Region by Normal Cumulative Distribution Function

The inclination of the plateau region is thought attributable to heterogeneity of the alloy phase. More specifically, the alloy has a distribution of regions which are different in α-β transformation pressure Pt, and the distribution results in an inclination of the plateau region. Such a distribution is due to heterogeneity of the composition and structure, grain boundary, vacancy, dislocation and like lattice defects, whereas it is almost impossible to individually model the influence of each of these causes.

Accordingly, the distribution is to be expressed by a probability density function, especially by a relatively simple normal probability density function. To express the asymmetry of the distribution, i.e., of the plateau region, the sum of two normal cumulative distribution functions which are different in mean value m and standard deviation σ is used as a basis for modeling the plateau region as represented by Equation 13 below.

$$X - X_\alpha = a_1 \cdot \phi_1 \left( \ln \frac{P}{P_0} ; m_1, \sigma_1 \right) + a_2 \cdot \phi_2 \left( \ln \frac{P}{P_0} ; m_2, \sigma_2 \right) \quad \text{(Equation 13)}$$

$$\phi = \frac{1}{\sqrt{2\pi}} \int_{-\infty}^{t} \exp\left[ -\frac{t^2}{2} \right] dt$$

$$t = \frac{\ln \frac{P}{P_0} - m}{\sigma}$$

$$m = \ln \frac{P_m}{P_0}$$

With reference to Equation 13, the hydrogen content $(X-X_\alpha)$ of the plateau region is expressed as frequency in a normal probability density function $$\frac{1}{\sqrt{2\pi}} \exp\left[ -\frac{t^2}{2} \right]$$

(mean m, standard deviation σ) as integrated wherein $\ln(P/P_0)$ is a random variable, i.e., normal cumulative distribution function φ.

As expressed by Equations 14 and 15, $a_1$ and $a_2$ are converted to fractions of two distribution functions which are 1 when combined together, and these fractions (weighting coefficients) are expressed as $f_1$ and $f_2$.

$$a_1 + a_2 = X_\beta - X_\alpha \quad \text{(Equation 14)}$$

$$f_1 = \frac{a_1}{X_\beta - X_\alpha} \quad \text{(Equations 15)}$$

$$f_2 = 1 - f_1$$

Consequently, the relation between the difference in hydrogen content $(X-X_\alpha)$ and the hydrogen pressure P is expressed by Equation 16 below wherein $f_1$, $f_2$, $\sigma_1$, $\sigma_2$, $m_1$ and $m_2$ are parameters, whereby the plateau region is modeled.

$$\begin{aligned} X - X_\alpha &= (X_\beta - X_\alpha)(f_1 \cdot \phi_1 + f_2 \cdot \phi_2) \quad \text{(Equation 16)} \\ &= \theta_{\alpha\beta} \left( \ln \frac{P}{P_0} ; f_1, f_2, \sigma_1, m_1, \sigma_2, m_2 \right) \end{aligned}$$

-continued

These parameters $f_1$, $f_2$, $\sigma_1$, $\sigma_2$, $m_1$ and $m_2$ are determined from measured values by the least square method. The probability density function thus obtained directly reflects the metallurgical heterogeneity of the alloy.

Overall Modeling

For modeling all the $\alpha$, $\beta$ and plateau regions, the function obtained from Equations 1 and 2 is divided into different cases according to the relation in magnitude between the pressure P and $\alpha$-$\beta$ transformation pressure Pt as expressed by Equations 17, 18 and 19, whereby Equation 20 is obtained.

$$X_A = \theta_\alpha \text{ for } P \leq P_t = X_\alpha \text{ for } P > P_t \quad \text{(Equation 17)}$$

$$X_B = 0 \text{ for } P \leq P_t = \theta_\beta - X_\beta \text{ for } P > P_t \quad \text{(Equation 18)}$$

$$X_{AB} = X - X_\alpha = \theta_{\alpha\beta} \quad \text{(Equation 19)}$$

$$X = X_A + X_{AB} + X_B \quad \text{(Equation 20)}$$

$$= X\left(\ln\frac{P}{P_0}; P_t, \Delta\mu_\alpha^\circ, X_{s,\alpha}, E_{HH,\alpha} \Delta\mu_\beta^\circ, X_{s,\beta},\right.$$

$$\left. E_{HH,\beta}, f_1, f_2, m_1, m_2, \sigma_1, \sigma_2, T\right)$$

Calculation for an optional temperature is done with consideration given to the temperature dependency of Pt, $Pm_1$ and $Pm_2$ according to van't Hoff relational expression as represented by Equations 21, 22 and 23 given below.

$$\ln\frac{Pt}{P_0} = \frac{\Delta Ht}{R} \cdot \frac{1}{T} + \frac{\Delta St}{R} \quad \text{(Equation 21)}$$

$$\ln\frac{P_{m1}}{P_0} = \frac{\Delta H_{m1}}{R} \cdot \frac{1}{T} + \frac{\Delta S_{m1}}{R} \quad \text{(Equation 22)}$$

$$\ln\frac{P_{m2}}{P_0} = \frac{\Delta H_{m2}}{R} \cdot \frac{1}{T} + \frac{\Delta S_{m2}}{R} \quad \text{(Equation 23)}$$

Accordingly, the eventual P-C-T isotherm involving temperature variations is to be represented by Equation 24.

(Equation 24)

$$X = X\left(\ln\frac{P}{P_0}; \Delta Ht, \Delta St, H_{\mu,\alpha}, S_{\mu,\alpha}, X_{s,\alpha}, H_{HH,\alpha},\right.$$

$$H_{\mu,\beta}, S_{\mu,\beta}, X_{s,\beta}, H_{HH,\beta}, S_{HH,\beta}, \beta, f_1, f_2, m_1,$$

$$\left. m_2, \sigma_1, \sigma_2, \Delta H_{m1}, \Delta S_{m1}, \Delta H_{m2}, \Delta S_{m2}, T\right)$$

However, for discriminating heterogeneity of the alloy phase, simulating systems, etc., useful results can be achieved even by merely modeling the plateau region.

Figure 2:
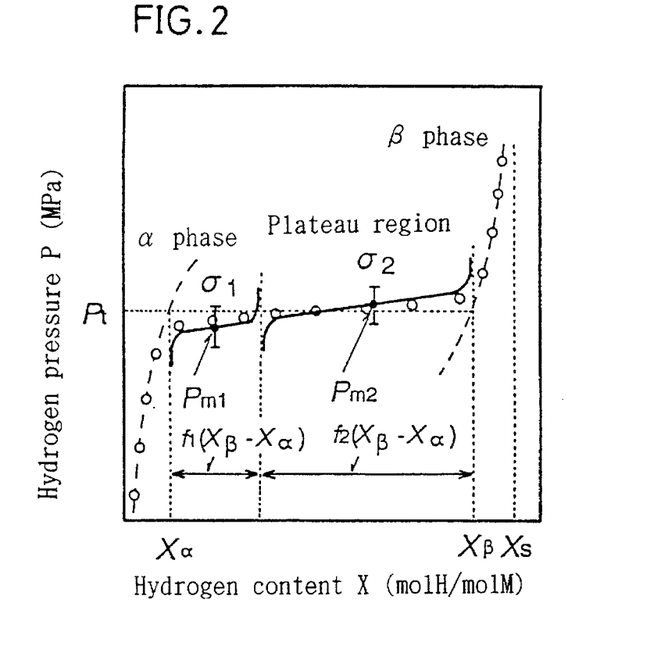
FIG. 2 is a P-C-T characteristics diagram showing two normal cumulative distribution functions to be used in the discriminating method for expressing the plateau region of the alloy.

FIG. 2 shows two normal cumulative distribution functions as individually plotted for representing a plateau region. Thus, the plateau region is expressed by the sum of the two functions, whereby satifactory fitting is realized although the plateau region exhibits P-C-T isotherms curving asymmetrically.

As to each of the aforementioned samples of hydrogen absorbing alloys, data was obtained by actual measurement and plotted on a graph like FIG. 2. The plotted result will be described below in comparison with the result obtained by modeling the plateau region based on the measured data and plotting the model as a curve on the same graph.

Figure 4:
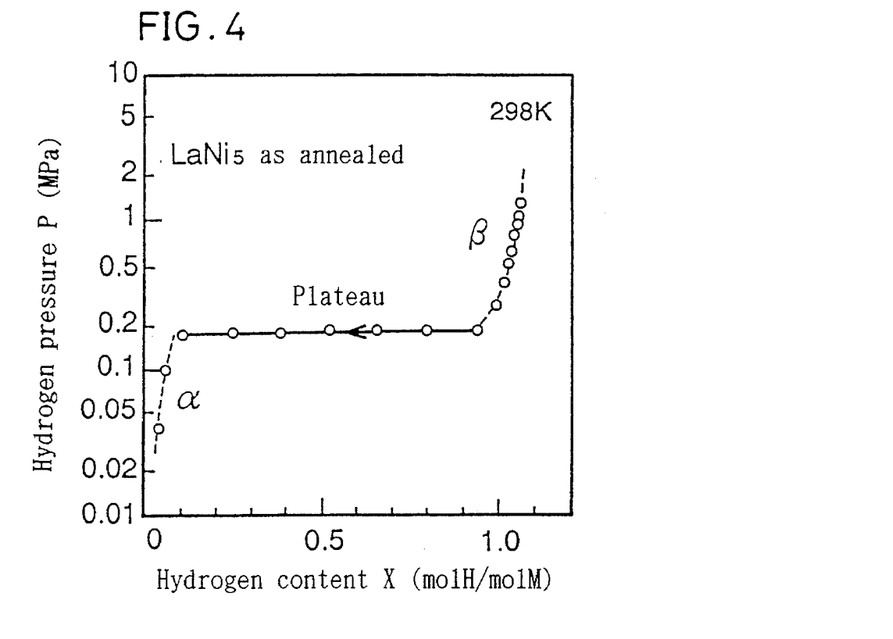
FIG. 4 is a P-C-T characteristics diagram showing the result obtained with the same sample as annealed.
Figure 5:
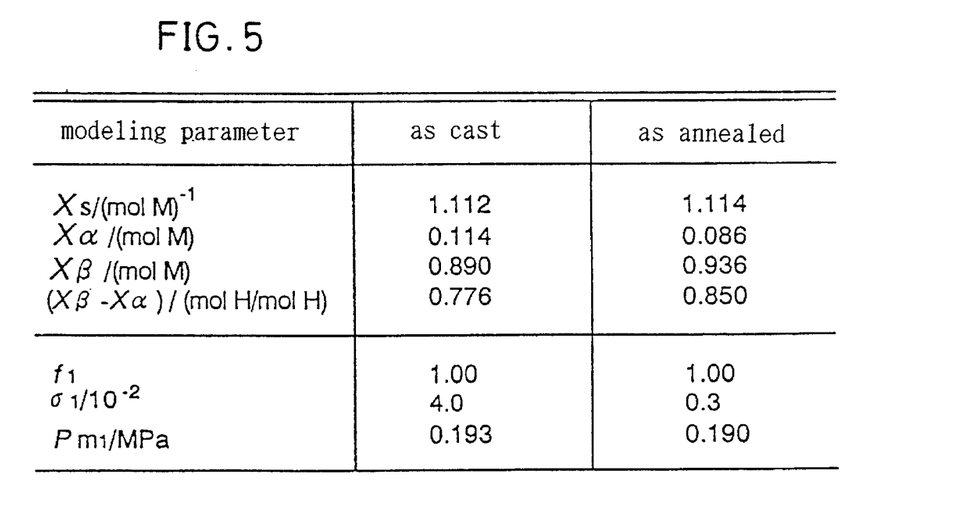
FIG. 5 is a table showing modeling parameters for the same sample.

FIGS. 3 and 4 show the results achieved by the two-component alloy LaNi$_5$ as cast and as annealed, respectively, the results including measured data and P-C-T isotherms. FIG. 5 shows modeling parameters of the two cases for comparison. The plateau region was modeled by one normal cumulative distribution function instead of the sum of two such functions.

The plateau region is represented by a solid-line portion of the P-C-T isotherm, and $\alpha$ and $\beta$ phase regions by broken-line portions thereof. These curve portions are all obtained by modeling.

As will be apparent from these drawings, the plateau region is modeled with satisfactory accuracy even with use of one normal cumulative distribution function. With the alloy not heat-treated (alloy as cast), the plateau region has a great inclination, whereas the heat-treated alloy (as annealed) has a substantially horizontal plateau region. The difference in the inclination of the plateau region is reflected by the standard deviation $\sigma$ of FIG. 5 which is 0.04 with the alloy as cast and which has decreased to 0.003 in the case of the alloy as annealed.

Although the inclination of the plateau region subjected to the heat treatment is thus very small and is not discernible with the unaided eye, the inclination can be quantitatively expressed in terms of standard deviation according to the discriminating method of the invention. This makes it possible to accurately recognize the effect of the heat treatment.

Figure 6:
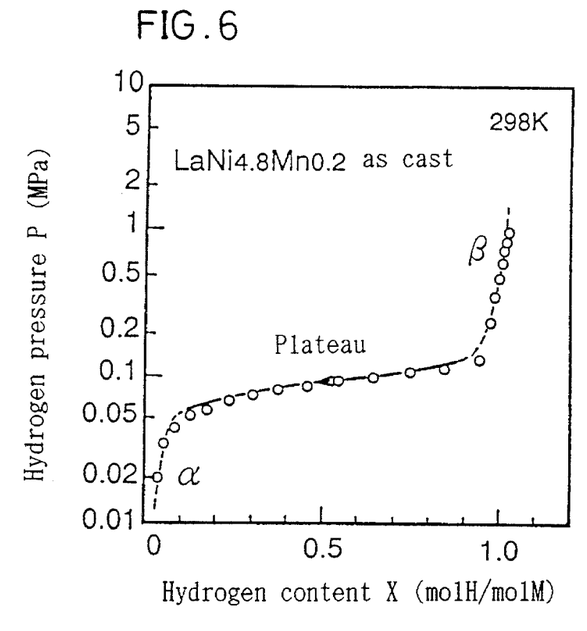
FIG. 6 is a P-C-T characteristics diagram showing the result obtained with a second sample as cast.
Figure 7:
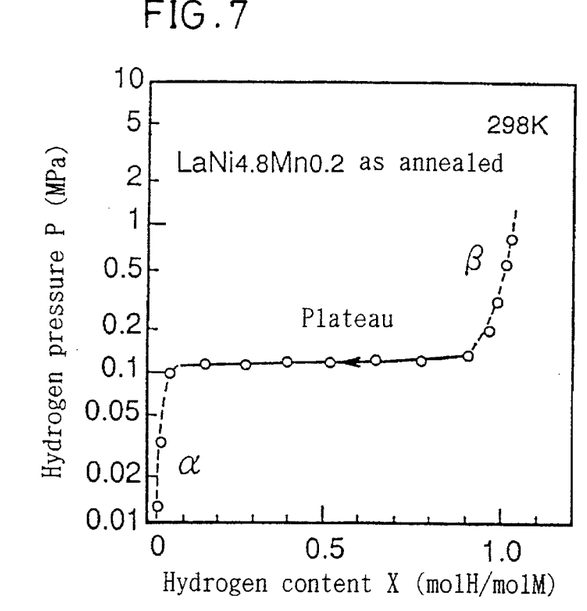
FIG. 7 is a P-C-T characteristics diagram showing the result obtained with the same sample as annealed.
Figure 8:
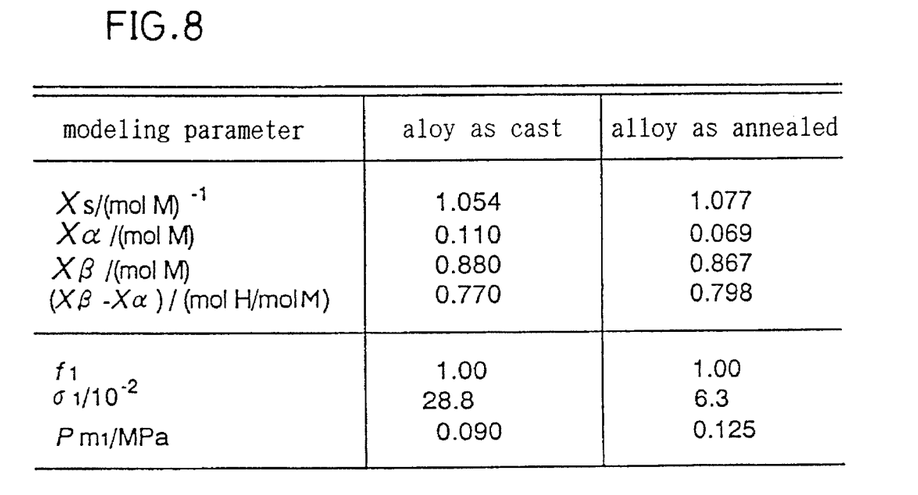
FIG. 8 is a table showing modeling parameters for the same sample.

FIGS. 6, 7 and 8 show the results achieved for the quasi two-component alloy LaNi$_{4.8}$Mn$_{0.2}$ by modeling with use of one normal cumulative distribution function.

Although satisfactory fitting is accomplished for the annealed alloy of FIG. 7, the measurements plotted in FIG. 6 for the alloy as cast are slightly deviated from a curve as modeled in the vicinity of the phase boundaries.

Figure 9:
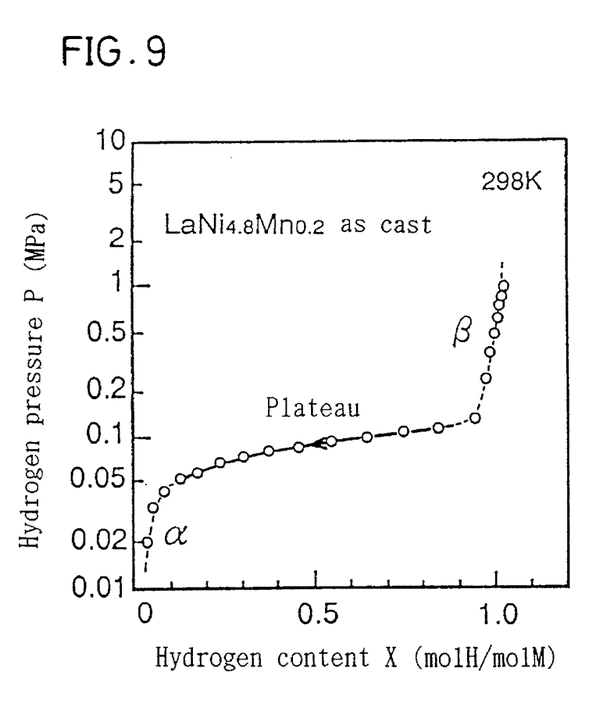
FIG. 9 is a P-C-T characteristics diagram showing the result of modeling with use of two normal cumulative distribution functions for the same sample.
Figure 10:
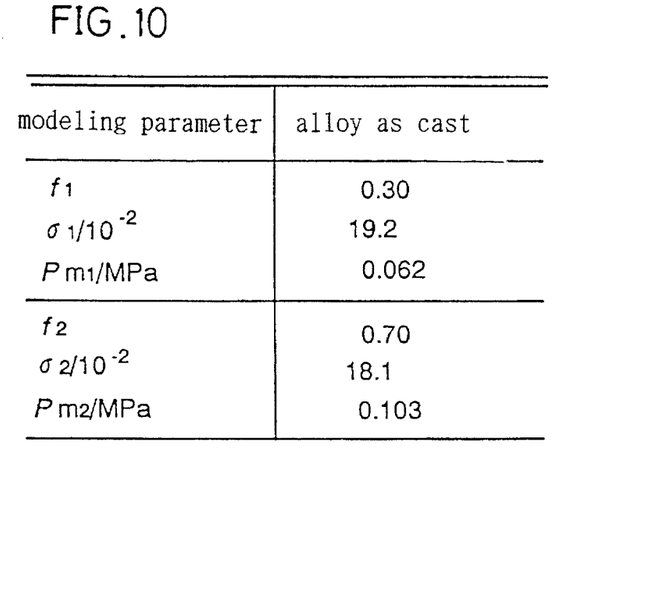
FIG. 10 is a table showing modeling parameters included in the two normal cumulative distribution functions.

Accordingly, two normal cumulative distribution functions were used for modeling for the same alloy LaNi$_{4.8}$Mn$_{0.2}$ as cast, whereby satisfactory fitting was accomplished as shown in FIG. 9. FIG. 10 shows the parameters used for the modeling. When the plateau region is represented by an asymmetric curve as shown in FIG. 9, modeling with two normal cumulative distribution functions is useful.

Figure 11:
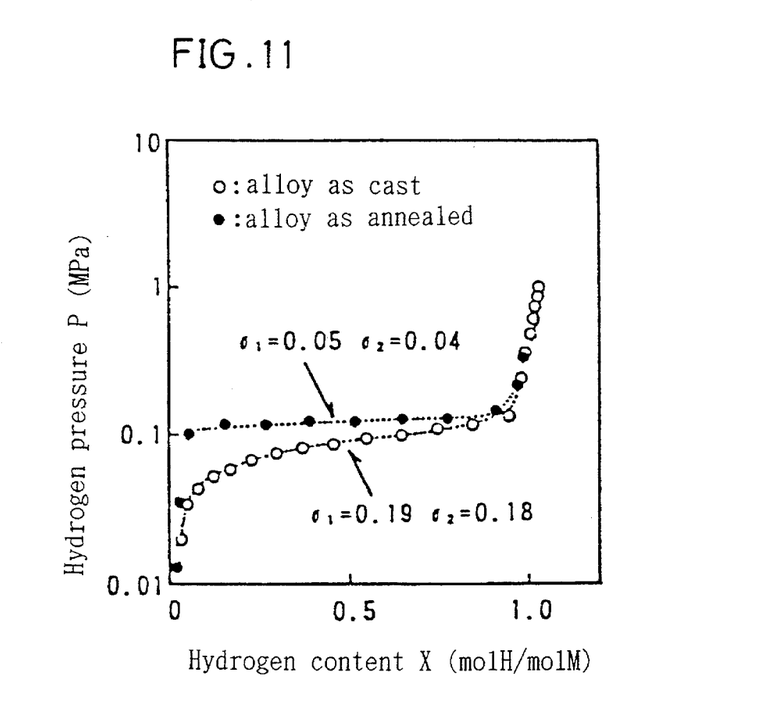
FIG. 11 is a P-C-T characteristics showing for comparison the standard deviations before and after annealing of the two normal cumulative distribution functions used for modeling.

Further FIG. 11 shows the results achieved by the quasi two-component LaNi$_{4.8}$Mn$_{0.2}$ as cast and as annealed for comparison in the case where the plateau region thereof was modeled with use of two normal cumulative distribution functions.

The heat treatment produces a remarkable effect as a decrease in the standard deviations $\sigma_1$ and $\sigma_2$ of the two functions.

EPMA revealed that the distribution of Mn in the composition was in match with the normal cumulative distribution function expressed by the parameters, substantiating that the standard deviation had physical significance in directly reflecting the heterogeneity of the alloy.

Figure 12:
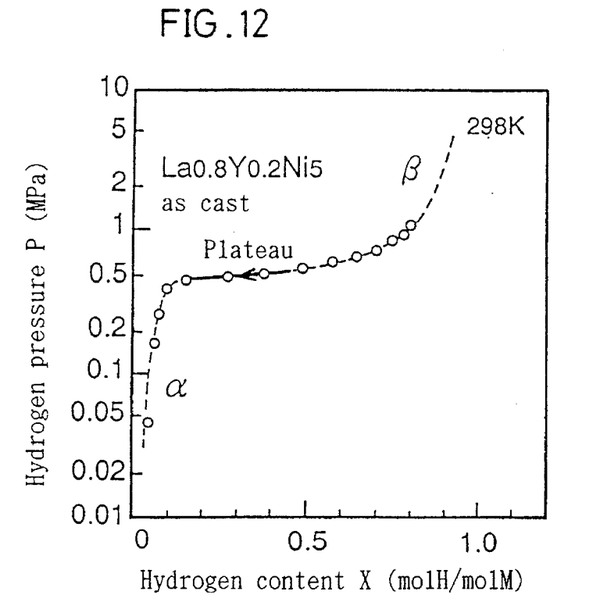
FIG. 12 is a P-C-T characteristics diagram showing the result obtained with a third sample as cast.
Figure 13:
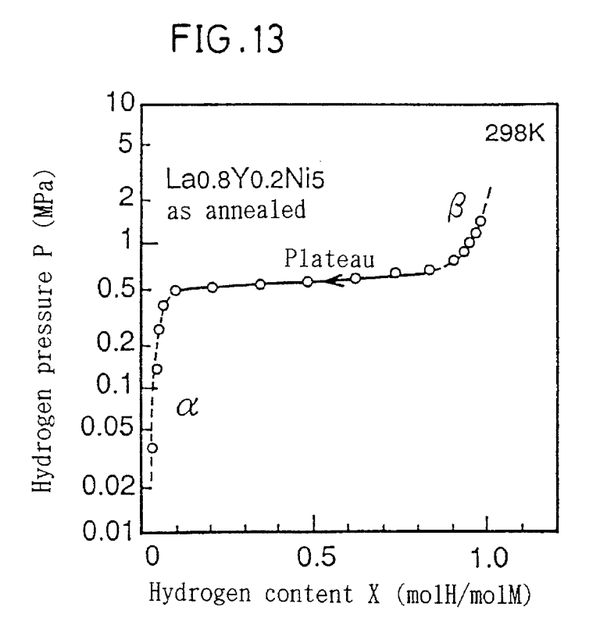
FIG. 13 is a P-C-T characteristics diagram showing the result obtained with the same sample as annealed.
Figure 14:
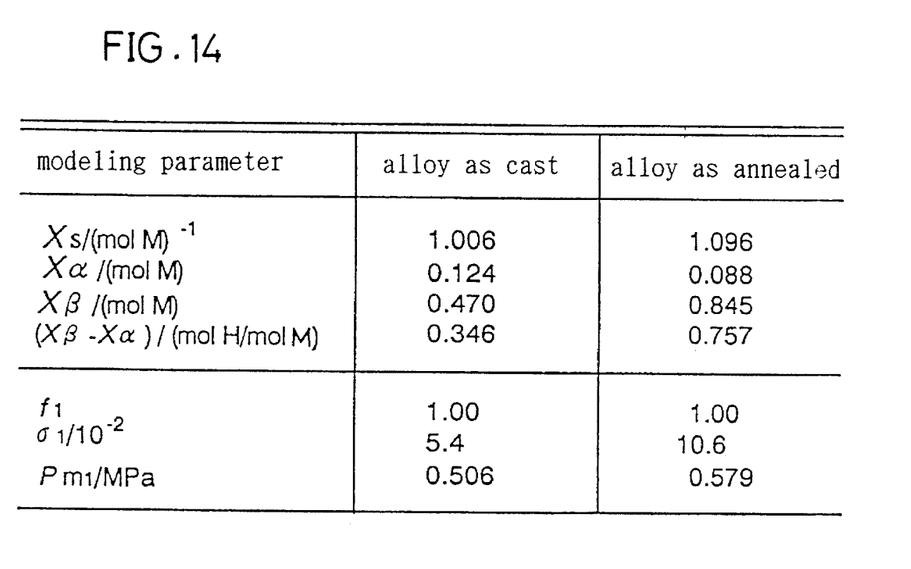
FIG. 14 is a table showing modeling parameters for the same sample.

FIGS. 12, 13 and 14 show the results achieved for the quasi two-component alloy La$_{0.8}$Y$_{0.2}$Ni$_5$ by modeling with use of one normal cumulative distribution function.

With the alloy as cast, observation of variations in the measured data plotted in FIG. 12 indicates that the hydrogen content at the $\beta$ phase boundary is 0.7 to 0.8, whereas the modeling parameters shown in FIG. 14 reveal that the hydrogen content at the $\beta$ phase boundary is 0.470.

Thus, the discriminating method of the present invention clearly indicates the phase boundary which is not discernible by the visual observation.

The result of FIG. 14 further shows that the heat treatment increased the width of the plateau region from 0.346 to 0.757 and that the standard deviation increased from 0.054 to 0.106. The effect of the heat treatment can therefore be quantitatively determined from the data in two different aspects.

EPMA has substantiated that the heat treatment makes the alloy more heterogeneous. This appears attributable to marked Ni segregation due to the heat treatment.

As described above, the method of the present invention for discriminating the equilibrium characteristics of hydrogen absorbing alloys makes it possible to model the plateau region, which is important to the characteristics of the alloy, with parameters having physical significance, and to quantitatively determine whether the equilibrium characteristics are acceptable using these parameters as evaluation criteria. The present method is not only useful for developing and evaluating hydrogen absorbing alloys per se but also applicable to a wide variety of fields for designing various systems incorporating the alloy, for simulation (e.g., heat output simulation in heat pumps) and for other purposes including quality control.

Further for use in hydrogen storage systems, the invention can be embodied as a device for calculating the hydrogen content from pressure and temperature measurements to detect and display the amount of remaining hyrogen.

The foregoing embodiments are given for the illustration of the present invention and should not be interpreted as limiting the invention as defined in the appended claims or reducing the scope thereof. The particulars of the invention are not limited to those of the above embodiments but can of course be modified variously by one skilled in the art without departing from the spirit of the invention as defined in the claims.

What is claimed is:

1. A method of producing a hydrogen absorbing alloy having desired equilibrium characteristics of a plateau region of the hydrogen absorbing alloy between a hydrogen solid solution region ($\alpha$ phase region) thereof and a metal hydride region ($\beta$ phase region) thereof, comprising the steps of:

(a) producing a hydrogen absorbing alloy;

(b) measuring the equilibrium hydrogen pressure and hydrogen content of the plateau region of the alloy;

(c) expressing the plateau region by a cumulative distribution function wherein the hydrogen content is taken as frequency and the equilibrium hydrogen pressure or a function thereof is taken as a random variable and determining a plurality of parameters defining the cumulative distribution function by numerical analysis of measured data as to the equilibrium hydrogen pressure and the hydrogen content;

(d) outputting the determined parameters;

(e) producing another alloy based on the determined parameters; and (f) repeating steps (a)–(d) until a hydrogen absorbing alloy having the desired equilibrium characteristics of the plateau region is obtained.

2. A method as defined in claim 1 wherein the cumulative distribution function is a normal cumulative distribution function, the logarithm of the equilibrium hydrogen pressure is taken as a random variable, and the standard deviation of the normal cumulative distribution function is used as an evaluation criterion.

3. A method as defined in claim 1 wherein the plateau region of the hydrogen absorbing alloy is expressed as a linear combination of a plurality of cumulative distribution functions.

4. A method as defined in claim 1 wherein boundaries between the plateau region of the hydrogen absorbing alloy and the hyrogen solid solution region and the metal hydride region thereof are determined by a regular solution model.

5. A method as defined in claim 1, wherein the equilibrium hydrogen pressure and the hydrogen content of the plateau region of the alloy are measured volumetrically.

6. A method of producing a hydrogen absorbing alloy having desired equilibrium characteristics of a plateau region of the hydrogen absorbing alloy between a hydrogen solid solution region ($\alpha$ phase region) thereof and a metal hydride region ($\beta$ phase region) thereof, comprising the steps of:

(a) producing a hydrogen absorbing alloy;

(b) measuring the equilibrium hydrogen pressure and hydrogen content of the plateau region of the alloy;

(c) expressing the plateau region by a cumulative distribution function wherein the hydrogen content is taken as frequency and the equilibrium hydrogen pressure or a function thereof is taken as a random variable and determining a plurality of parameters defining the cumulative distribution function by numerical analysis of measured data as to the equilibrium hydrogen pressure and the hydrogen content;

(d) outputting the determined parameters;

(e) producing another alloy based on the determined parameters and repeating steps (b)–(d); and (f) optionally repeating step (e) until a hydrogen absorbing alloy having the desired equilibrium characteristics of the plateau region is obtained.

7. A method as defined in claim 6, wherein the alloy produced based on the determined parameters is an annealed alloy.

* * * * *